(12) United States Patent
Kanner et al.

(10) Patent No.: US 9,265,919 B2
(45) Date of Patent: Feb. 23, 2016

(54) SIMPLIFIED MEDICAL INFLATION DEVICE WITH PASSIVE LATCH

(71) Applicant: Atrion Medical Products, Inc., Arab, AL (US)

(72) Inventors: Rowland W. Kanner, Guntersville, AL (US); Brian A. Roberts, Owens Cross Roads, AL (US)

(73) Assignee: Atrion Medical Products, Inc., Arab, AL (US)

( * ) Notice: Subject to any disclaimer, the term of this patent is extended or adjusted under 35 U.S.C. 154(b) by 196 days.

(21) Appl. No.: 14/016,988

(22) Filed: Sep. 3, 2013

(65) Prior Publication Data

US 2014/0081205 A1   Mar. 20, 2014

Related U.S. Application Data

(60) Provisional application No. 61/702,936, filed on Sep. 19, 2012, provisional application No. 61/722,435, filed on Nov. 5, 2012.

(51) Int. Cl.
*A61M 25/10* (2013.01)
*F15B 15/26* (2006.01)

(52) U.S. Cl.
CPC ..... *A61M 25/1018* (2013.01); *A61M 25/10184* (2013.11); *A61M 25/10187* (2013.11); *F15B 15/261* (2013.01)

(58) Field of Classification Search
CPC ....... F15B 15/24; F15B 15/261; F15B 15/267
USPC ...................................... 92/18, 15
See application file for complete search history.

(56) References Cited

U.S. PATENT DOCUMENTS

| | | | | |
|---|---|---|---|---|
| 1,799,017 A * | 3/1931 | Junghans | | 74/576 |
| 4,668,220 A * | 5/1987 | Hawrylenko | | 604/155 |
| 4,723,938 A * | 2/1988 | Goodin et al. | | 604/97.02 |
| 4,765,559 A * | 8/1988 | Crisp | | 242/384.2 |
| 4,838,864 A | 6/1989 | Peterson | | |
| 4,919,121 A * | 4/1990 | Rydell et al. | | 604/97.03 |
| 4,940,459 A * | 7/1990 | Noce | | 604/97.02 |
| 5,472,424 A * | 12/1995 | Lampropoulos et al. | | 604/97.03 |
| 5,713,242 A | 2/1998 | Kanner et al. | | |
| D454,358 S | 3/2002 | Davis et al. | | |
| 6,796,959 B2 | 9/2004 | Davis et al. | | |
| 6,938,319 B2 | 9/2005 | Davis et al. | | |
| 8,191,457 B2 | 6/2012 | Kanner et al. | | |

(Continued)

*Primary Examiner* — Thomas E Lazo
(74) *Attorney, Agent, or Firm* — Clark Hill PLC; James R. Foley

(57) ABSTRACT

An inflator which preferably has a gauge thereon and means for communicating with a medical connector or device. The inflator has a syringe body, a handle on the syringe body, a plunger which extends out from the handle and extends into the syringe body, and a plunger locking mechanism which is associated with the handle. The plunger locking mechanism includes an actuation lever which is configured to be depressed, thereby causing the plunger locking mechanism to actuate. The plunger locking mechanism includes a ratchet pawl which is configured to selectively engage corresponding ratchet structure, thereby locking the plunger in place, during which time the plunger is prevented from being retracted, but can still be advanced (i.e., pushed into the syringe body during pressurization). The plunger locking mechanism is configured such that when the actuation lever is released, the ratchet pawl disengages from the corresponding ratchet structure, thus freeing the plunger.

19 Claims, 18 Drawing Sheets

(56) References Cited

U.S. PATENT DOCUMENTS

| | | | |
|---|---|---|---|
| 8,412,310 B2* | 4/2013 | Liu et al. | 600/432 |
| 8,490,770 B2* | 7/2013 | Schwekutsch et al. | 192/219.5 |
| 8,499,681 B2 | 8/2013 | Kanner et al. | |
| 2010/0191184 A1* | 7/2010 | Choi | 604/117 |
| 2013/0261601 A1* | 10/2013 | Webler | 604/509 |
| 2013/0268049 A1* | 10/2013 | Munsinger et al. | 623/1.11 |
| 2014/0005630 A1* | 1/2014 | Bagaoisan et al. | 604/500 |

* cited by examiner

SIMPLIFIED MEDICAL INFLATION DEVICE WITH PASSIVE LATCH

RELATED APPLICATIONS (PRIORITY CLAIM)

This application claims the benefit of U.S. Provisional Application Ser. No. 61/702,936, filed Sep. 19, 2012, and U.S. Provisional Application Ser. No. 61/722,435, filed Nov. 5, 2012, both of which are hereby incorporated by reference in their entirety.

BACKGROUND

The present invention generally relates to inflation devices which are configured to deliver fluid to a medical balloon catheter, working fluid under pressure and to monitor that pressure during therapeutic procedures such as balloon sinuplasty, a procedure to expand and permanently dilate sinus passages within a mammalian body.

Inflation devices such as the devices shown in, for example, U.S. Pat. Nos. 4,838,864 and 6,796,959, may be used in such procedures; however, the robust locking mechanism used to engage a plunger for high pressure development on these type of inflators, while intuitive to hospital catheter laboratory personnel familiar with such devices, have proven to be challenging to some medical personnel unfamiliar with hospital catheter lab procedures. These inflation devices are configured such that they are typically provided with one of two types of plunger engagement: either plunger initially engaged thus requiring active disengagement by the user, or plunger initially disengaged requiring active engagement by the user. Further, pressurization is subsequently accomplished via the user having to rotate the plunger in order to advance its screw type mechanism forward, thereby delivering fluid and building pressure.

Medical providers in hospital catheter laboratory settings are generally highly trained with regard to how to use such complicated inflation devices. However, some medical procedures, such as balloon sinuplasty, are not always conducted in a hospital catheter laboratory setting. Instead, such procedures are often performed at less costly environments, such as the office of an ENT doctor where both doctors and their assisting nurses have not necessarily had the extensive training and experience of catheter laboratory technicians.

A simpler operating inflation device that is more intuitive and requires less training is therefore more desirable for such applications. Standard syringes are a common every day item within all medical care settings, and medical staffs universally understand their operation without additional training.

SUMMARY

An object of an embodiment of the present invention is to provide an inflator which is easy to use, arguably as easy to use as a standard syringe.

Briefly, an embodiment of the present invention provides an inflator which has a syringe body, a handle on the syringe body, a plunger which extends out from the handle and extends into the syringe body, and a plunger locking mechanism which is associated with the handle. The plunger locking mechanism includes an actuation lever which is configured to be depressed, thereby causing the plunger locking mechanism to actuate. The plunger locking mechanism includes a ratchet pawl which is configured to selectively engage corresponding ratchet structure, thereby locking the plunger in place, during which time the plunger is prevented from being retracted, but can still be advanced (i.e., pushed into the syringe body during pressurization). The plunger locking mechanism is configured such that when the actuation lever is released, the ratchet pawl disengages from the corresponding ratchet structure, thus freeing the plunger.

BRIEF DESCRIPTION OF THE DRAWINGS

The organization and manner of the structure and operation of the invention, together with further objects and advantages thereof, may best be understood by reference to the following description taken in connection with the accompanying drawings wherein like reference numerals identify like elements in which.

DESCRIPTION OF ILLUSTRATED EMBODIMENTS

Figure 1:
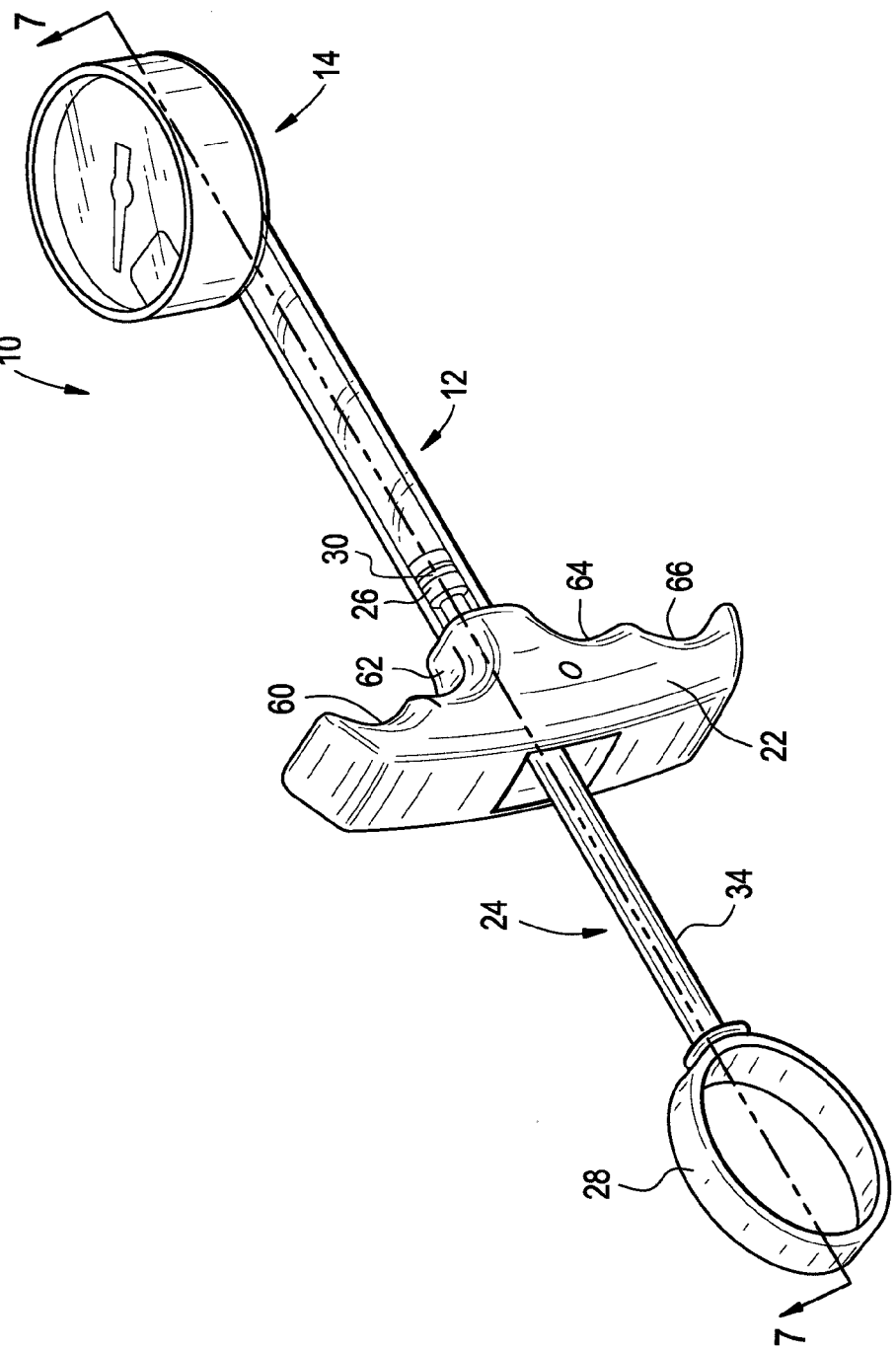
FIG. 1 is a perspective view of an inflator, wherein the inflator is in accordance with a first embodiment of the present invention, showing a plunger of the inflator in a loaded position.

While this invention may be susceptible to embodiment in different forms, there are shown in the drawings and will be described herein in detail, specific embodiments with the understanding that the present disclosure is to be considered an exemplification of the principles of the invention, and is not intended to limit the invention to that as illustrated.

FIGS. 1-6 illustrate an inflator 10 which is in accordance with a first embodiment of the present invention. The inflator 10 includes a syringe body 12 which is configured to engage a pressure gauge 14 at its end 16. Preferably, that same end 16 of the syringe body 12 is also configured to engage a delivery hose 18 which has a Luer connector 20 at its end. Alternatively or additionally, the syringe body 12 can be configured to directly receive the Luer connector 20 without having to use the hose 18. Regardless of whether a hose 18 is used, the Luer connector 20 can be engaged with a medical device which is to be inflated, such as a dilation balloon. Although the present description uses sinuplasty as an example application, other procedures where the inflator 10 would serve well include discography, a non-balloon direct injection procedure, and the injection of stem cell material into mammalian bodies for tissue regeneration or repair.

The syringe body 12 extends from, and is connected to, a handle 22. A plunger 24 extends through the handle 22 into the syringe body 12. The plunger 24 has a piston 26 on one end thereof, and a plunger ring 28 is provided at its opposite end. Preferably, a seal 30 is provided on the piston 26, for sealing against an internal wall 32 of the syringe body 12. Between the plunger ring 28 and the end of the plunger 24 extends a rod-like portion 34. The rod-like portion 34 of the plunger 24 preferably includes a ratchet surface, i.e. a plunger ratchet 36.

A plunger locking mechanism 40 is provided in association with the handle 22 for selectively engaging the plunger ratchet 36 and locking the plunger 24 in place relative to the syringe body 12, with regard to retraction of the plunger 24, while allowing the plunger 24 to be pushed in (i.e., during pressurization). Preferably, the plunger locking mechanism 40 is a single piece which provides that it is normally and naturally out of engagement with the plunger ratchet 36, thereby providing that the plunger 24 is free to be pushed into (advanced) and pulled out of (retracted) the syringe body 12. The plunger locking mechanism 40 provides an actuation lever 42 which is accessible by a user, whereby pressing the actuation lever causes the plunger locking mechanism 40 to pivot about pivot point 44. The plunger locking mechanism 40 also has portions which are fully within the handle 22 (where the handle 22 is preferably multi-piece and, when pieced together, is effectively hollow). Other portions of the plunger locking mechanism 40 include a ratchet pawl 46 which is inside the handle 22, and which is configured to engage the plunger ratchet 36, thereby locking the plunger 24 in place relative to retraction of the plunger 24 but allowing advancement of the plunger 24 (i.e., for pressurization).

Figure 10:
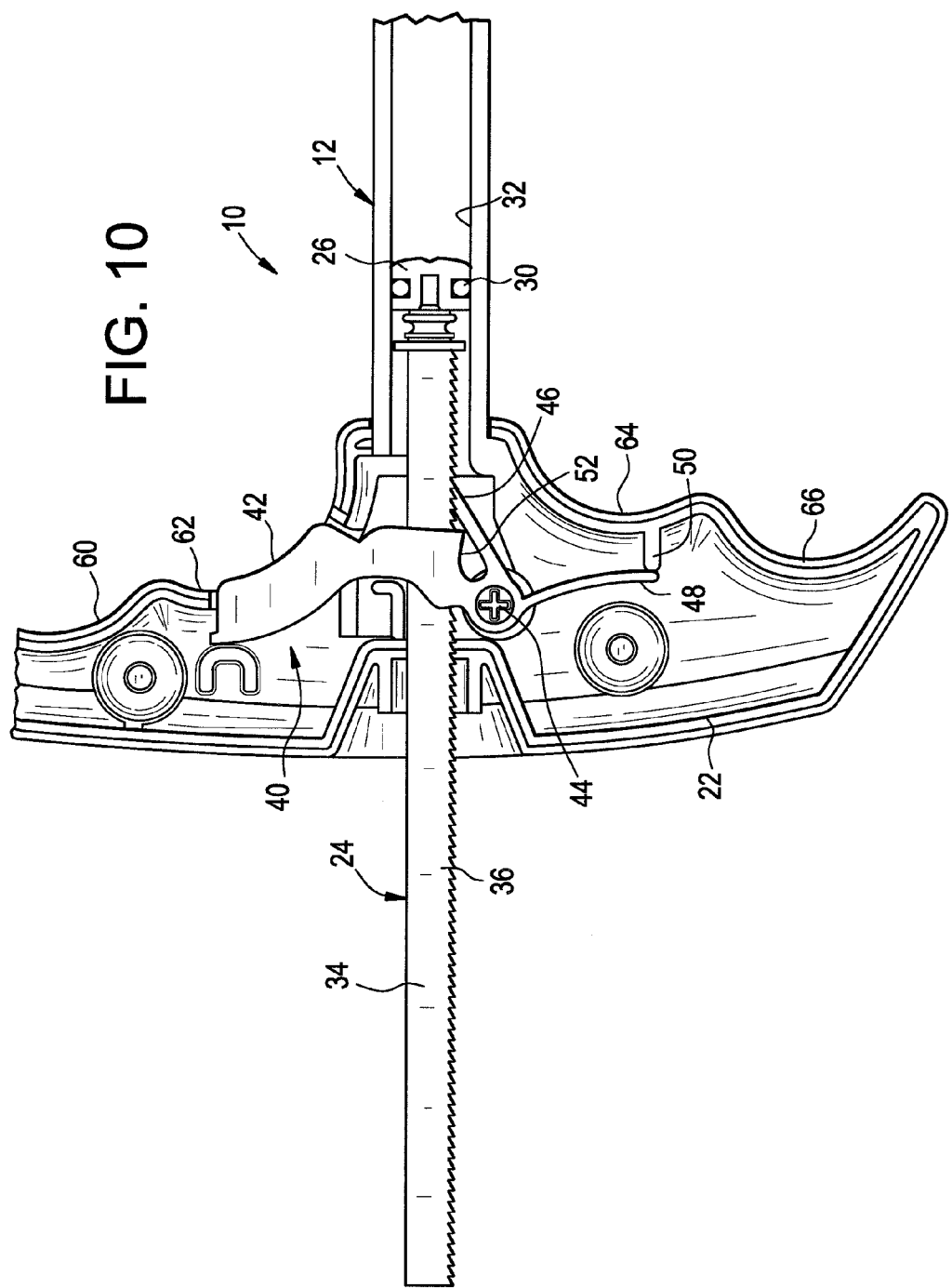
FIG. 10 shows the plunger locking mechanism after an actuation lever of the plunger locking mechanism has been depressed, showing a ratchet pawl of the plunger locking mechanism engaged with the plunger and a return spring of the plunger locking mechanism deflected under load.

The plunger locking mechanism 40 also includes an integral lever return spring 48. As shown in FIG. 10, when the actuation lever 42 is pressed, causing the plunger locking mechanism 40 to pivot about pivot point 44, the integral lever return spring 48 is configured to engage an internal wall 50 or other suitable surface of the handle 22, which causes the integral lever return spring 48 to deflect, effectively urging the ratchet pawl 46 away from the plunger ratchet 36 should the user release the actuation lever 42. The plunger locking mechanism 40 also includes a pawl disengagement heel 52 which works to push against the ratchet pawl 46 and assist moving the ratchet pawl 46 away from the plunger ratchet 36 upon release of the actuation lever 42.

Figure 2:
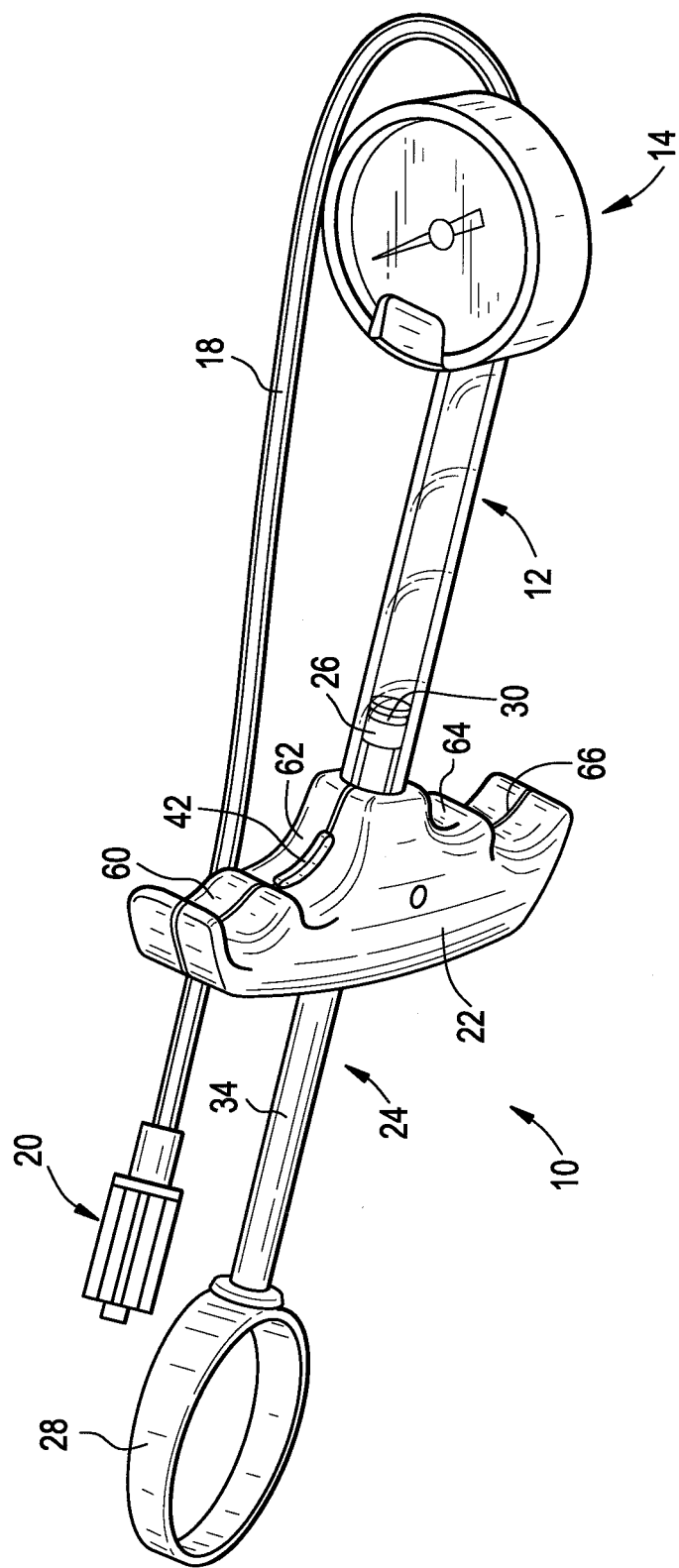
FIG. 2 is another perspective view of the inflator, showing the inflator engaged with a hose and Luer.

With regard to an outside contour of the handle 22, as shown in FIG. 2, preferably the handle 22 includes a plurality of indentations 60, 62, 64, 66 for engagement by the fingers of a user. Specifically, preferably the handle 22 includes a first indentation 60, a second indentation 62, a third indentation 64, and a fourth indentation 66. Preferably, the actuation lever 42 of the plunger locking mechanism 40 is provided in the second indentation 62.

In use, the inflator 10 provides that fluid and pressure are delivered by depressing the plunger ring 28 with a thumb of one's hand, while opposing fingers are braced against indentations of the handle 22. This is very much like a typical injection syringe. As such, operation is therefore very familiar to all medically trained personnel.

Typically, balloons for an ENT procedure require less pressure than those used in cardiovascular or peripheral balloon procedures. Through appropriate sizing of the piston 26 at the end of the plunger 24 (and appropriate sizing of the diameter of the syringe body 12 itself), the necessary pressure (usually a maximum of 12 atmospheres (176.4 psi)) can be obtained with the force of one hand, delivering between 8 to 14 pounds of force against the plunger 24. Ergonomic studies have shown this amount of force to be well within the capability of even a normal, 5th percentile human female operator.

Balloon dilation procedures commonly require that fluid pressure be maintained within the balloon for a period of time in order to adequately move the tissue required to achieve lasting results from the dilation process. This is not a problem when inflators with screw type mechanisms are employed as previously described above; however, holding this pressure with the unaided hand for the necessary period as one would with a common syringe can become fatiguing for doctors and nurses when only a bare hand must be relied upon to sustain required balloon pressures.

To provide an improved device, the inflator 10 includes the plunger locking mechanism 40. The plunger locking mechanism 40 is passive in that it is normally not deployed, but becomes automatically deployed whenever the user's thumb has engaged the plunger ring 28, and a user's finger has engaged the actuation lever 42 of the plunger locking mechanism 40, in preparation for pressure generation. When the actuation lever 42 of the plunger locking mechanism 40 is depressed, the plunger locking mechanism 40 pivots about pivot point 44, causing the ratchet pawl 46 of the plunger locking mechanism 40 to engage the plunger ratchet 36 on the plunger 24, thereby locking the plunger 24 in place as shown in FIG. 10. In this position, the plunger 24 is prevented from retracting, but the plunger 24 can be advanced (pushed in) to increase pressurization. Once achieved, maximum balloon dilation pressure can be sustained for an extended period of time, for example ten seconds or more, without user fatigue simply by maintaining minimal force against the actuation lever 42 of the plunger locking mechanism 40.

Figure 8:
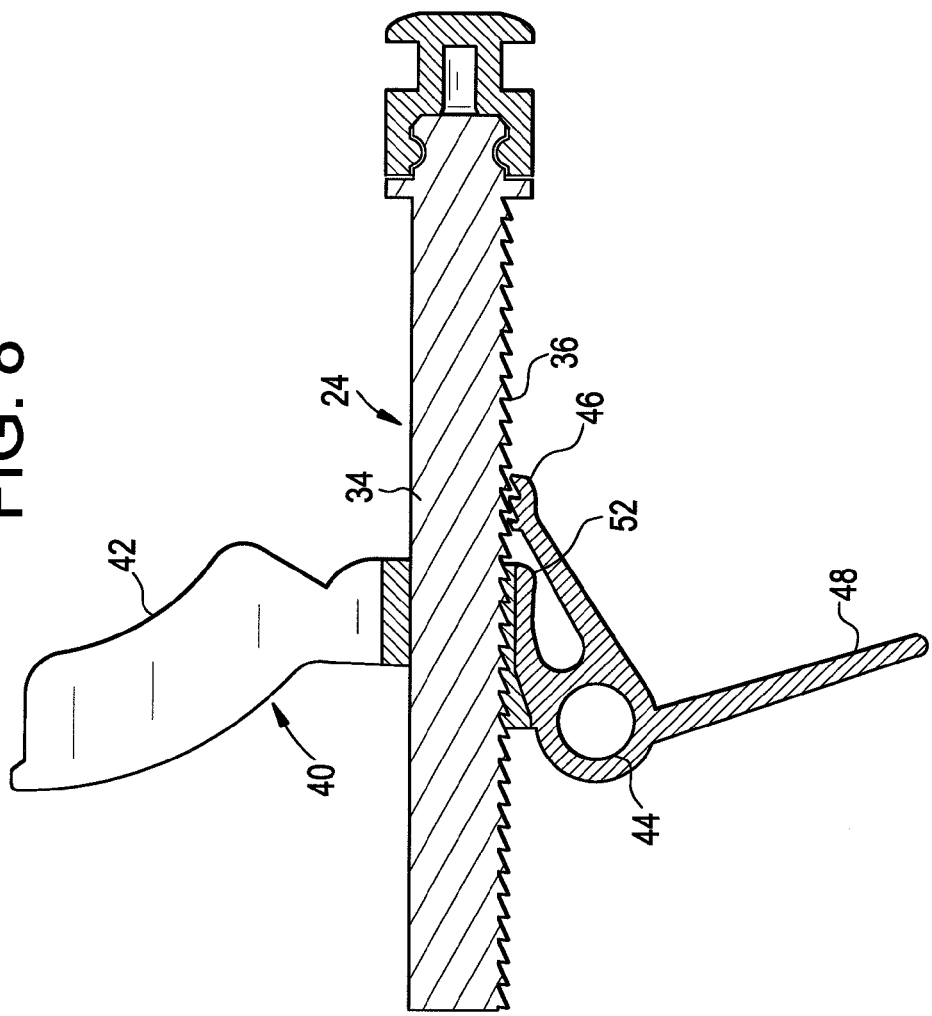
FIG. 8 is a enlarged view of a portion of the inflator, specifically a plunger locking mechanism, and a portion of the plunger including a piston on its end.
Figure 9:
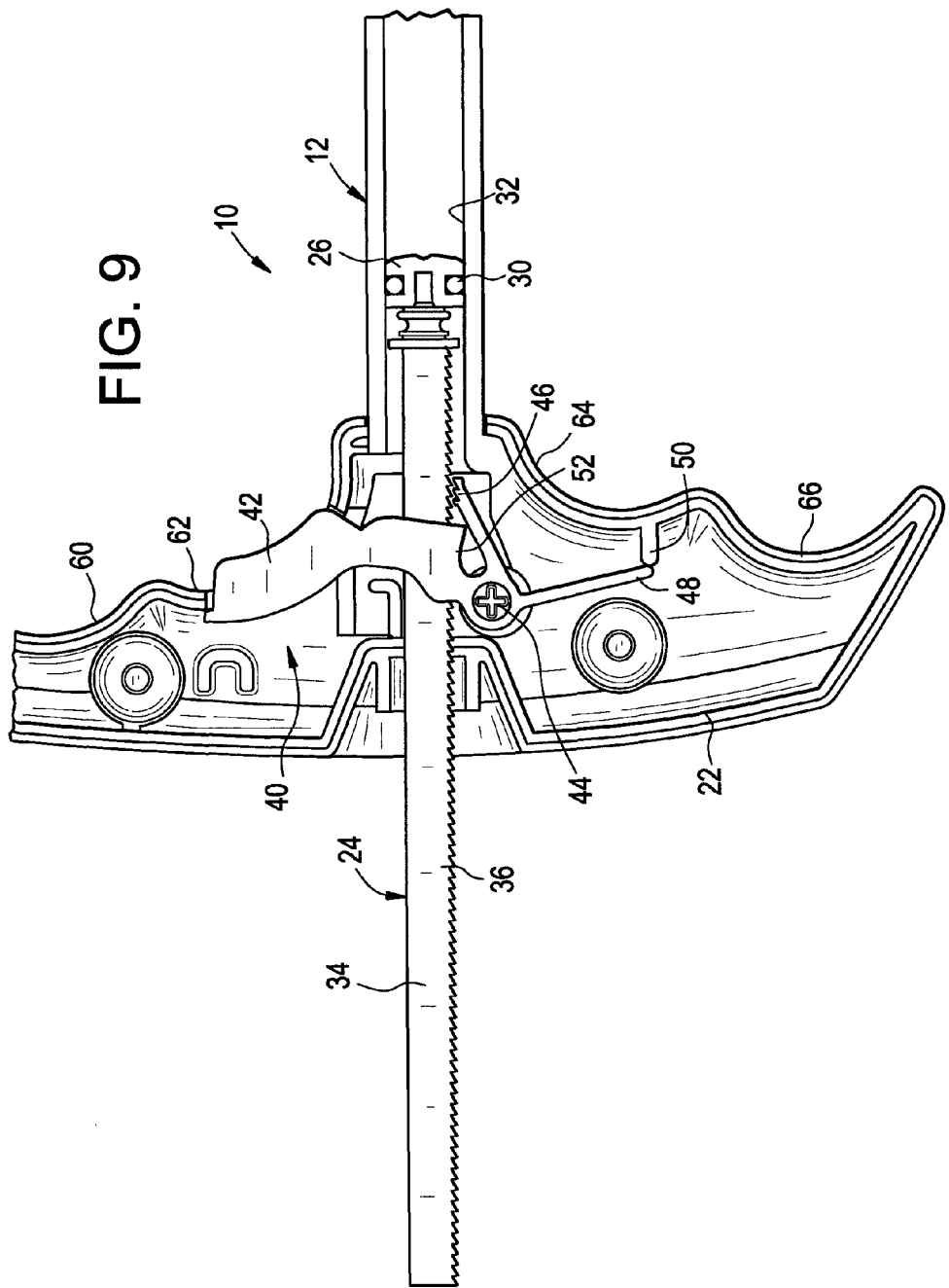
FIG. 9 shows the plunger locking mechanism in a released and at rest position.

As shown in FIG. 10, in addition to the deflectable leaf spring mounted ratchet pawl 46 of the plunger locking mechanism 40 engaging the plunger ratchet 36, the integral lever return spring 48 engages a wall or other surface 50 in the handle 22, causing the integral lever return spring 46 to deflect. Upon releasing the actuation lever 42 of the plunger locking mechanism 40, the integral lever return spring 48 (see FIGS. 8-10) provides the necessary force to restore the actuation lever 42 to its unlocked position as shown in FIG. 9. In order to overcome load-induced friction of the engaged plunger ratchet 36, and assure release of the ratchet pawl 46 from the plunger 24, the plunger locking mechanism 40 is provided with a ratchet pawl disengagement heel 52, which works to push against the deflectable leaf spring mounted ratchet pawl 46 and assist moving the ratchet pawl 46 away from the plunger 24.

Figure 7:
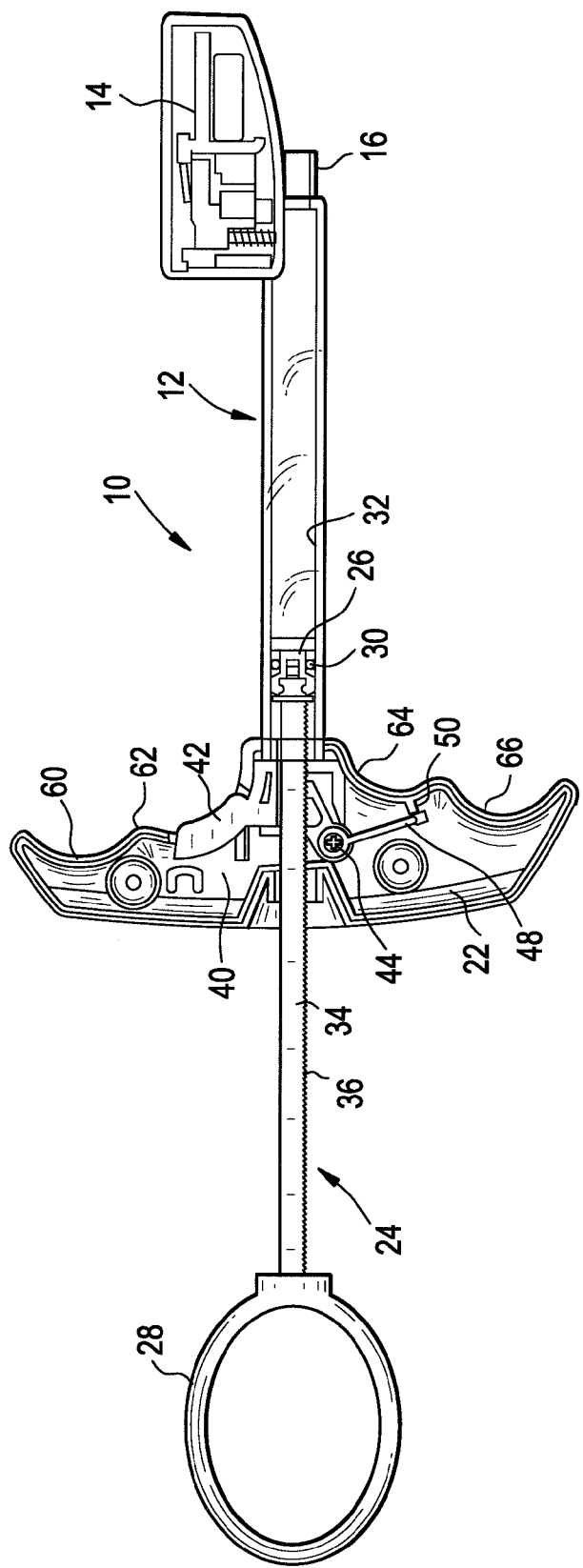
FIG. 7 is a section view of the inflator, taken along line 7-7 of FIG. 1, showing internal components of the inflator.

Each finger of the human hand contributes non-proportional strength to the hand's overall grip, with the second finger generally being the strongest at an average of 37.5% of the entire hand's grip and the third finger contributing on average 28.7%. Therefore, these two fingers constitute an average of 66.2% of a human hand's grip which opposes the thumb. Preferably, the handle 22 of the inflator 10 is configured, positioned and angled to take advantage of a user's hand and its strength by locating the plunger ring 28 in the thumb's natural location whenever the second and third fingers of a user's hand engage the handle's innermost of four finger receiving indentations 62, 64, immediately on either side of the syringe body 12. Holding the inflator 10 upright, as shown in FIG. 7, to allow reading of its gauge 14, naturally places the user's second finger in the second indentation 62 (in which the actuation lever 42 of the plunger locking mechanism 40 is located), above the syringe body 12, and against the actuation lever 42, and naturally places the user's third finger in the third indentation 64, immediately below the syringe body 12. In this position, a user's first finger naturally falls into the first indentation 60, and their fourth finger falls into the fourth indentation 66. Should a user wish to use two hands to operate the inflator 10 instead of one, a user can do so by placing their second finger of one hand in the first indentation 60, their third finger in the third indentation 64, and then on the other side of the handle 22, positioning their opposite hand with its second finger in the second indentation 62, their third finger in the fourth indentation 66, and both thumbs within the plunger ring 28 (said thumbs being naturally extended in that direction). Each hand would therefore only need to deliver half the force to achieve desired system pressure.

For balloon inflation purposes, a fluid such as saline may be used to fill the inflator's syringe body 12. Preparation of the inflator and catheter system generally involves filling to about 80% of fluid capacity to allow reserve for achieving a good vacuum of, for example 20 in. Hg or more, in order to fully draw down the balloon for repositioning or removal from the patient after dilation. However, some users may choose to fill the inflator completely full if such a reserve is not desired.

Figure 11:
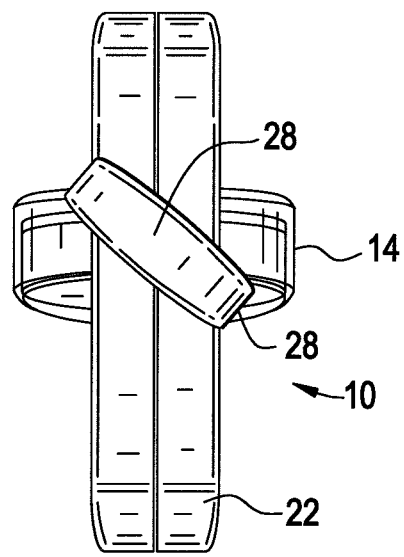
FIG. 11 is an end view of the inflator, similar to the end view which is shown in FIG. 6, but showing the plunger ring after is has been rotated in order to lock the inflator.

Preferably, the inflator 10 is configured to provide a locking feature to facilitate balloon deflations. To achieve full balloon deflation following an extended balloon inflation period, the plunger ring 28 may be grasped with a finger, pulled to its fully distal position and the plunger 24 locked in that position by rotating the plunger ring 28 forty-five to ninety degrees as shown in FIG. 11. This distal locking feature relieves the user of having to manually hold the plunger 24 in position for the duration of time necessary to achieve full deflation, and frees them entirely to proceed with other aspects of the procedure such as balloon repositioning or removal from the patient.

With regard to the structure which provides this type of locking feature, one possibility is to provide the plunger 24 as having either a "rectangular" or "D" shaped cross-section, wherein one flat (or the only flat) in the "D" shape is faced with the plunger ratchet 36. Preferably, the plunger 24 extends out of the handle 22 through a close fitting, correspondingly shaped (i.e., either a rectangular or "D"-shaped) hole. Preferably, the far end of the plunger 24 (i.e., the end proximate the piston 26) is cylindrical, with the outside diameter being either the smallest dimension of the rectangular plunger section or, in the case of the "D" shape, of a diameter that when concentric with the with the radius of the "D" form, does not rise up beyond the flat of the "D" form. This cylindrical shape is preferably provided as being long enough such that when the plunger 24 is pulled fully back proximally in the vacuum mode, the beginning of the rectangle or the "D" form of the plunger 24 occurs just outside of the receiving hole in the back of the handle 22. Thereafter, rotating the plunger 24 (via the plunger ring 28) causes the distal corners of the rectangular form or "D" shape to span the minor dimension of the receiving hole in the handle 22, thereby effectively hooking the plunger there, out of registration, until the plunger 24 is rotated back into registration with the receiving hole. In the case of a plunger 24 having a rectangular cross-section, a stop may be provided on a ledge of the handle in order to prevent rotation of the plunger 24 more than, for example, ninety degrees, in order to assure that the plunger ratchet 36 returns to the correct side (i.e., facing the ratchet pawl 46 once the plunger 24 is pushed in). However, a "D" shaped plunger would only go back one way, as such a stop would arguably not be needed.

Figure 12:
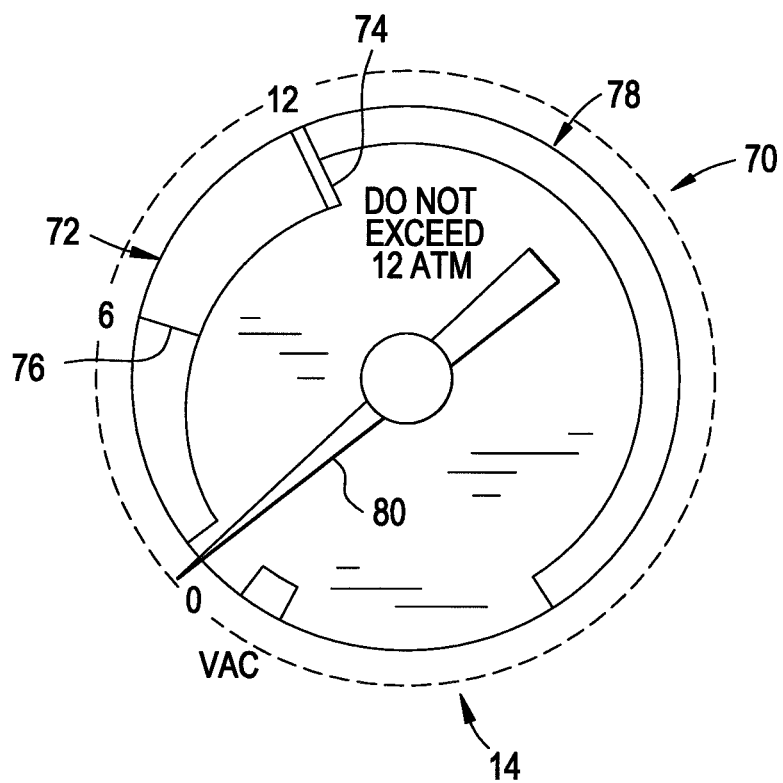
FIG. 12 illustrates a gauge dial face which can be provided on a gauge which is engaged with the inflator, such as the gauge which is depicted in the previous Figures.
Figure 13:
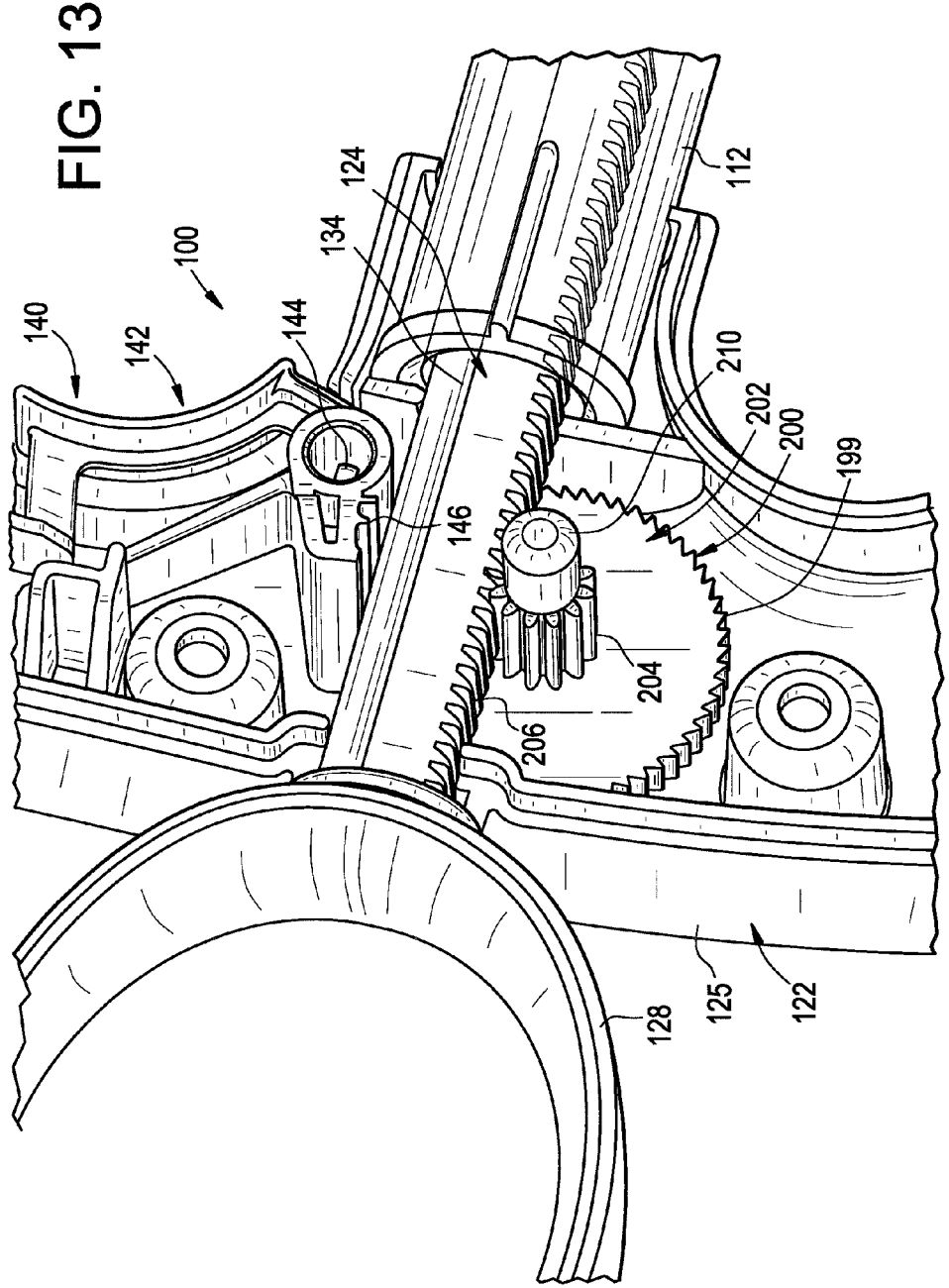
FIG. 13 illustrates a portion of an inflator, wherein the inflator is in accordance with an alternative embodiment of the present invention, showing the inflator with a right half of a handle component of the inflator removed.
Figure 14:
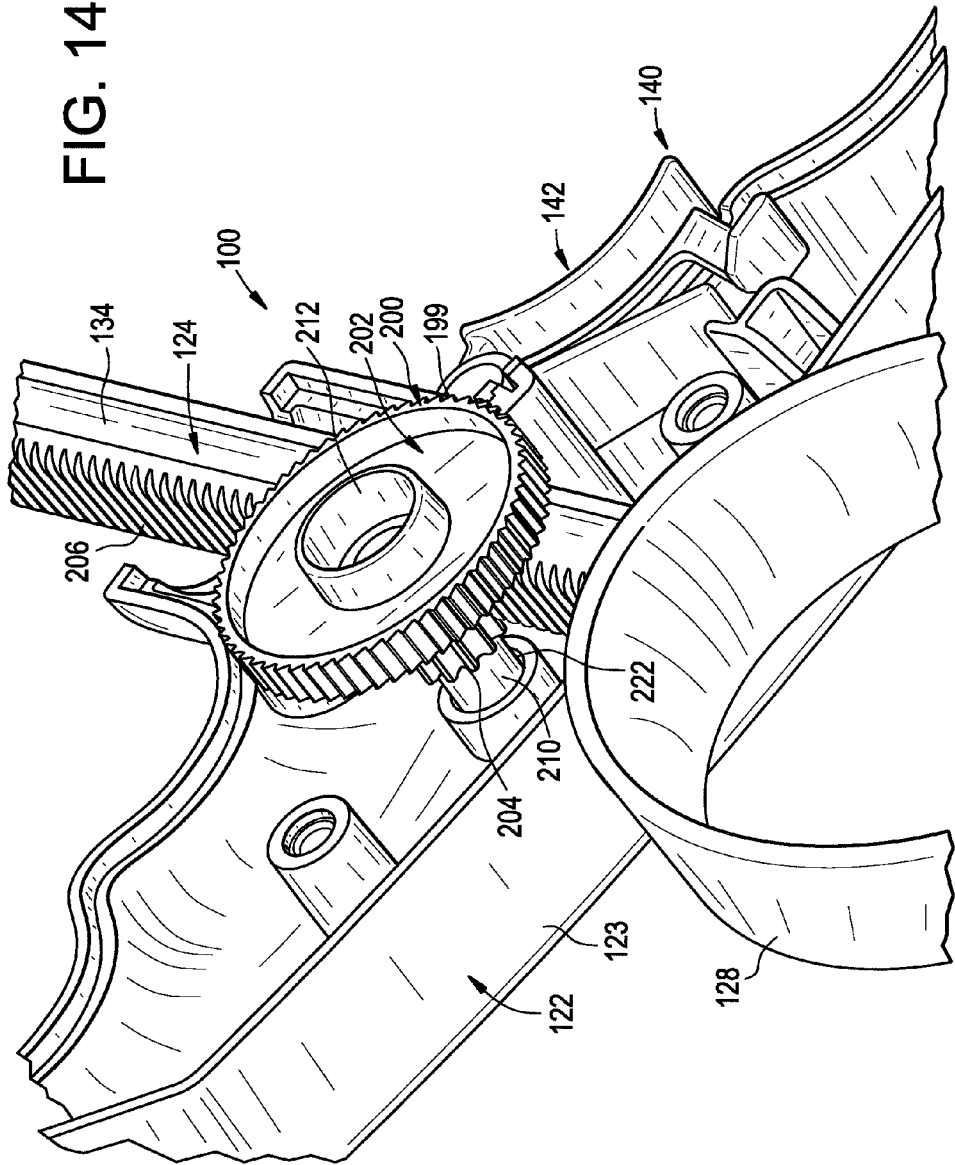
FIG. 14 is similar to FIG. 13, but showing the inflator with a left half of the handle removed.

In the interest of simplifying the training required for users, a unique gauge dial face 70 such as that which is illustrated in FIG. 12 can be used (i.e., used in association with the gauge 14 shown in previous Figures). As shown in FIG. 12, the gauge dial face 70 offers a green area 72 with the target pressure 74 clearly identified, an intermediate pressure mark 76 and a red area 78 above the target pressure 74 to clearly define this range as the pressure area that shall not be entered. Users need only be instructed to watch the gauge needle 80, take it to the target pressure mark 74, and not enter into the red zone 78 beyond. Other colors may be substituted in these locations as desired for the application intended.

As discussed above, although the present description uses sinuplasty as an example application, other procedures where the inflator 10 would serve well include discography, a non-balloon direct injection procedure, and the injection of stem cell material into mammalian bodies for tissue regeneration or repair.

Figure 15:
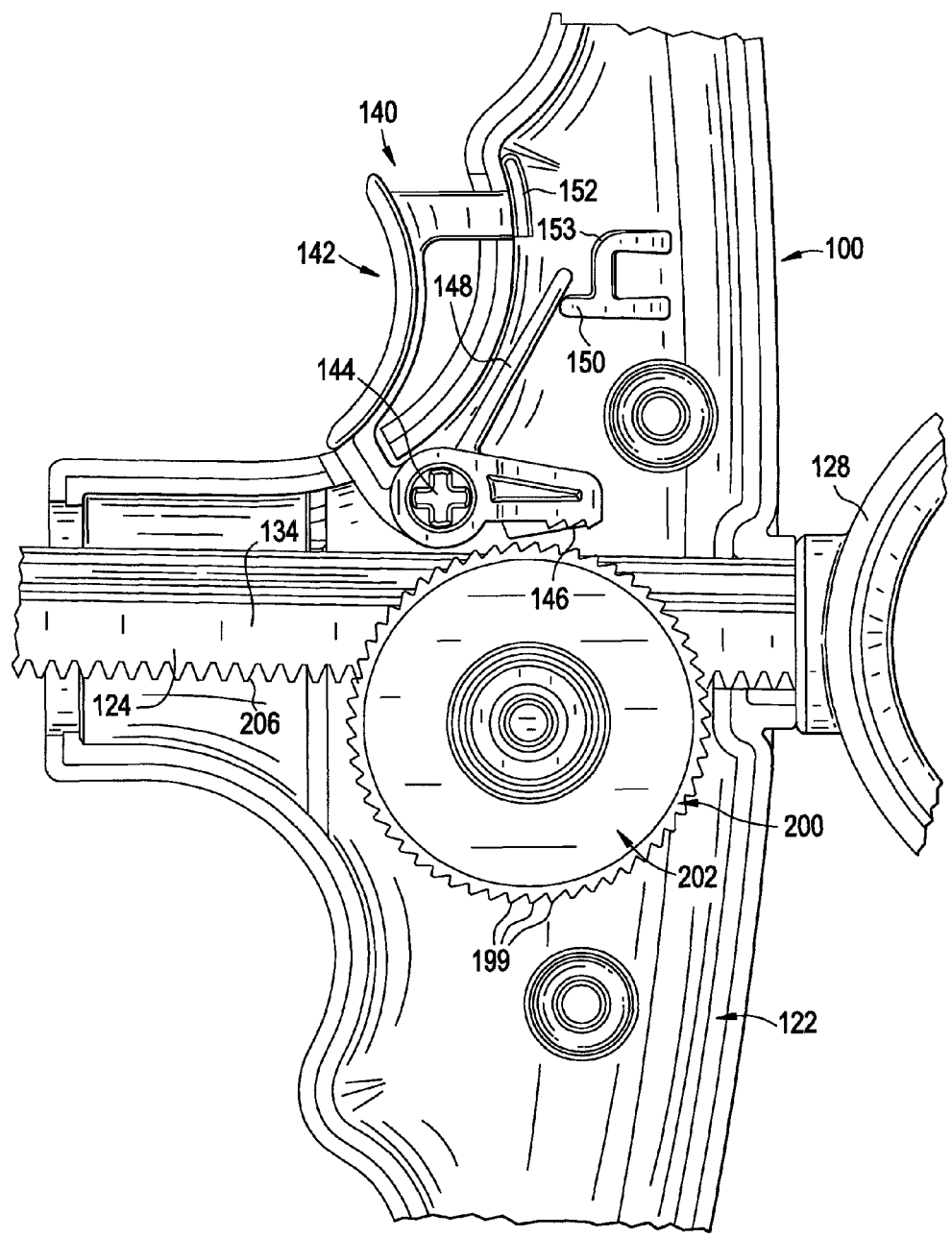
FIG. 15 shows the inflator of FIGS. 13 and 14 in the condition when an actuation lever of the inflator is not depressed or actuated.
Figure 16:
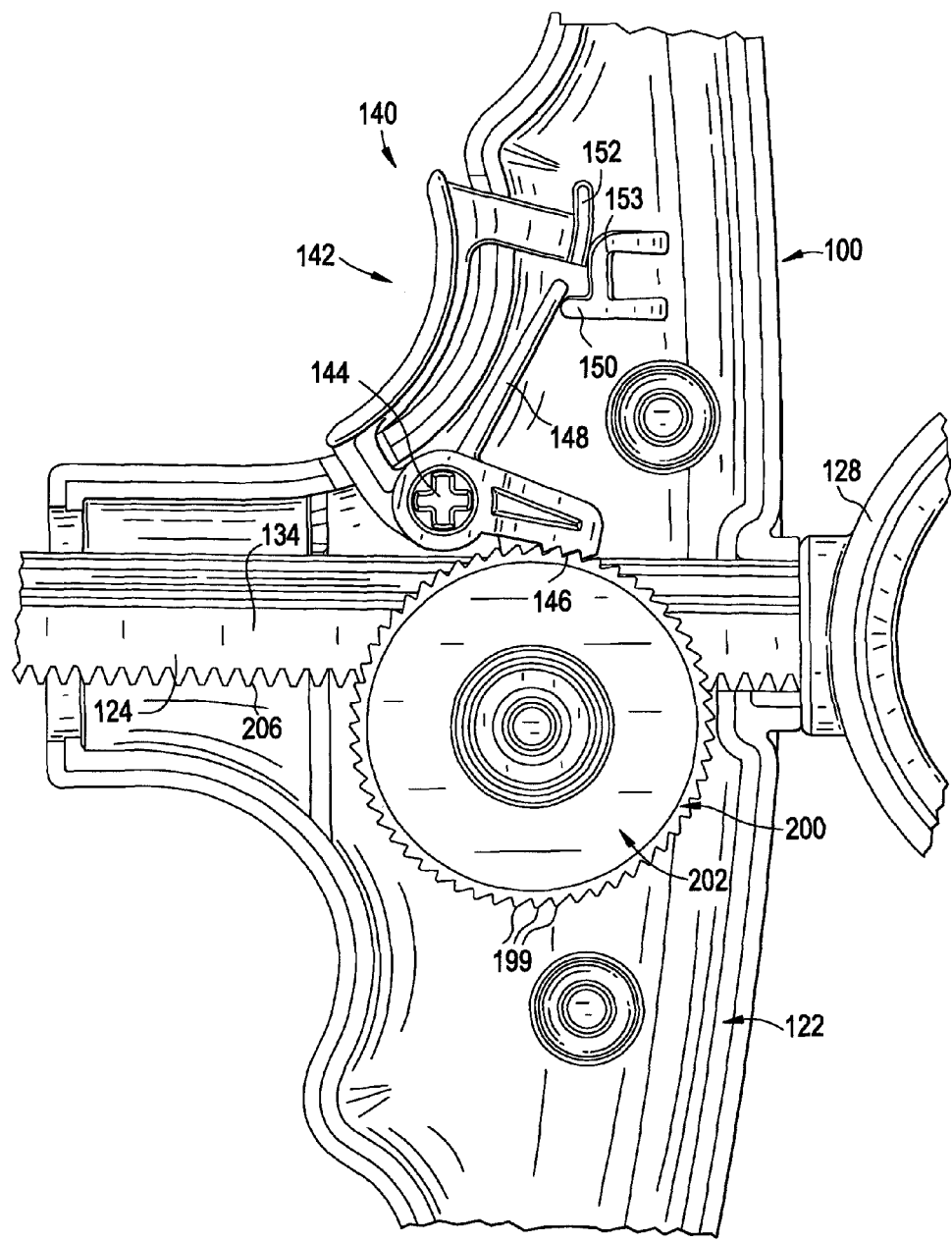
FIG. 16 is similar to FIG. 15, but shows the inflator in the condition when the actuation lever is depressed or actuated.

FIGS. 13-19 illustrate an inflator 100 which is in accordance with an alternative embodiment of the present invention. While there are many similarities between the inflator 10 and the inflator 100, the inflator 100 is directed at providing a greater number of ratchet engagement points over the length of the plunger's travel and a reduction of the load received by the ratchet pawl while holding the plunger at pressure. To provide this advantage, instead of having a ratchet pawl 46 engage the plunger 24 directly (as is provided by inflator 10), as shown in FIG. 16, the inflator 100 provides that a ratchet pawl 146 engages a ratchet wheel 200 of a geared ratchet 202, and that a pinion 204 of the geared ratchet 202 is what engages the plunger 124 (see FIG. 13).

Figure 3:
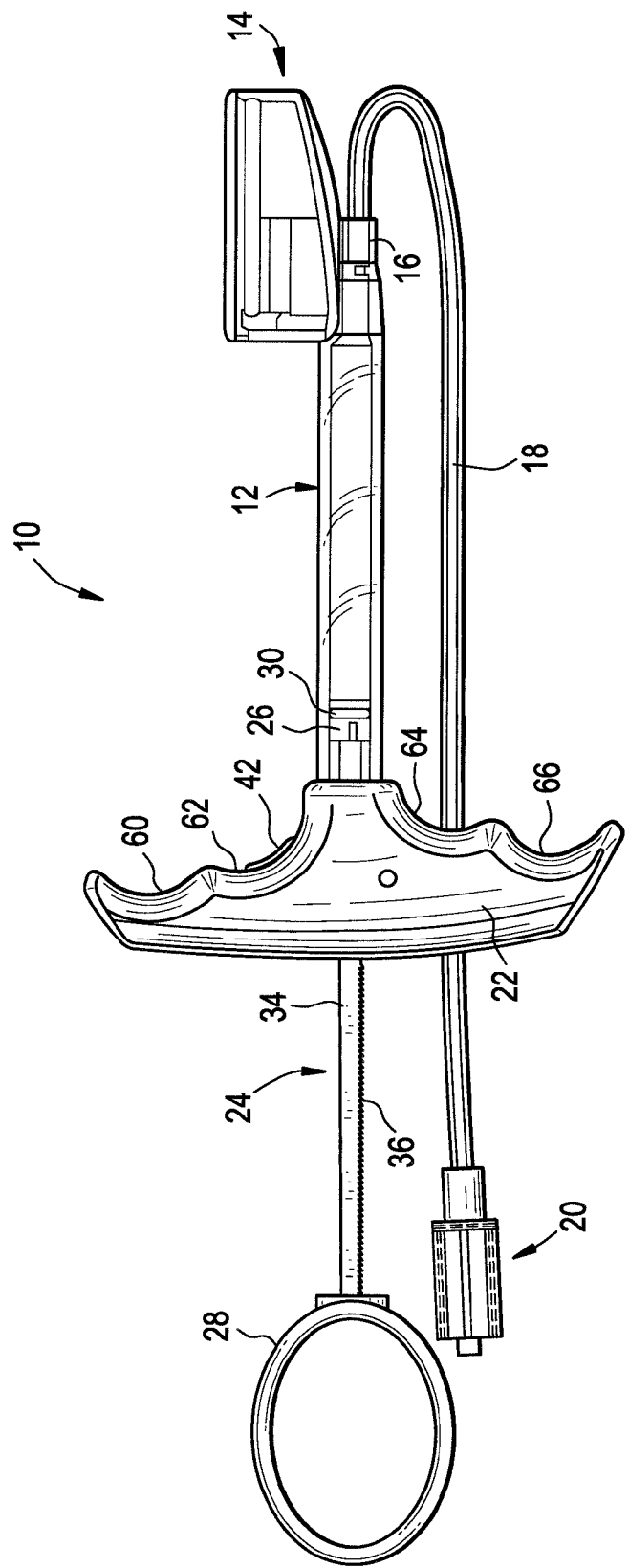
FIG. 3 is a side view of the inflator.
Figure 4:
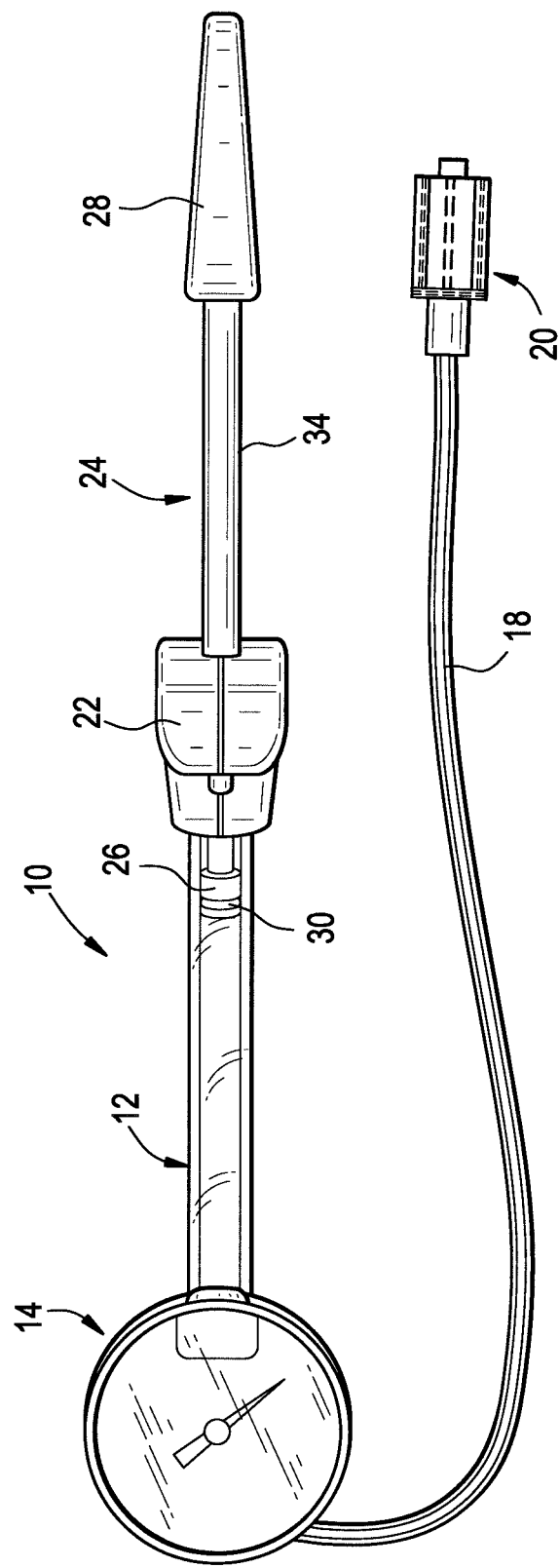
FIG. 4 is a top view of the inflator.
Figure 5:
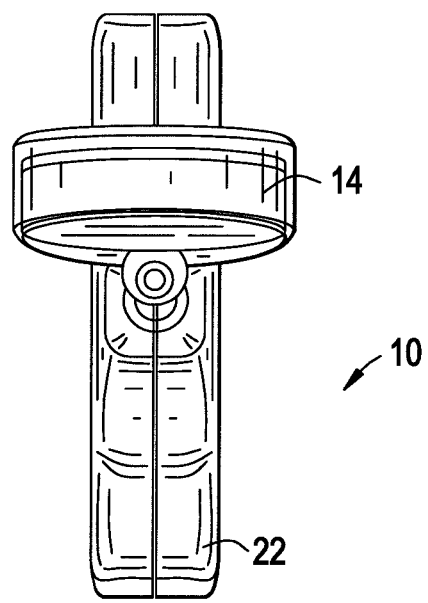
FIG. 5 is an end view of the inflator, said end being from a gauge end of the inflator.
Figure 6:
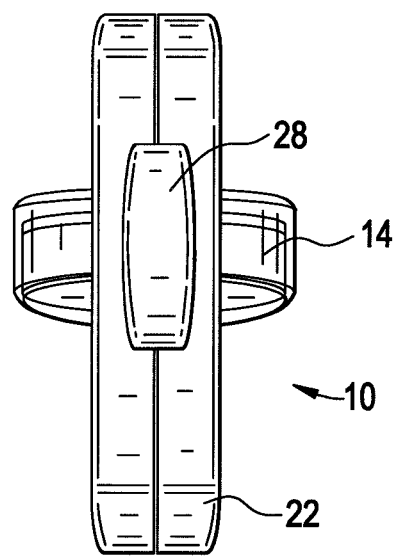
FIG. 6 is another end view of the inflator, said end being from a plunger ring end of the inflator.
Figure 17:
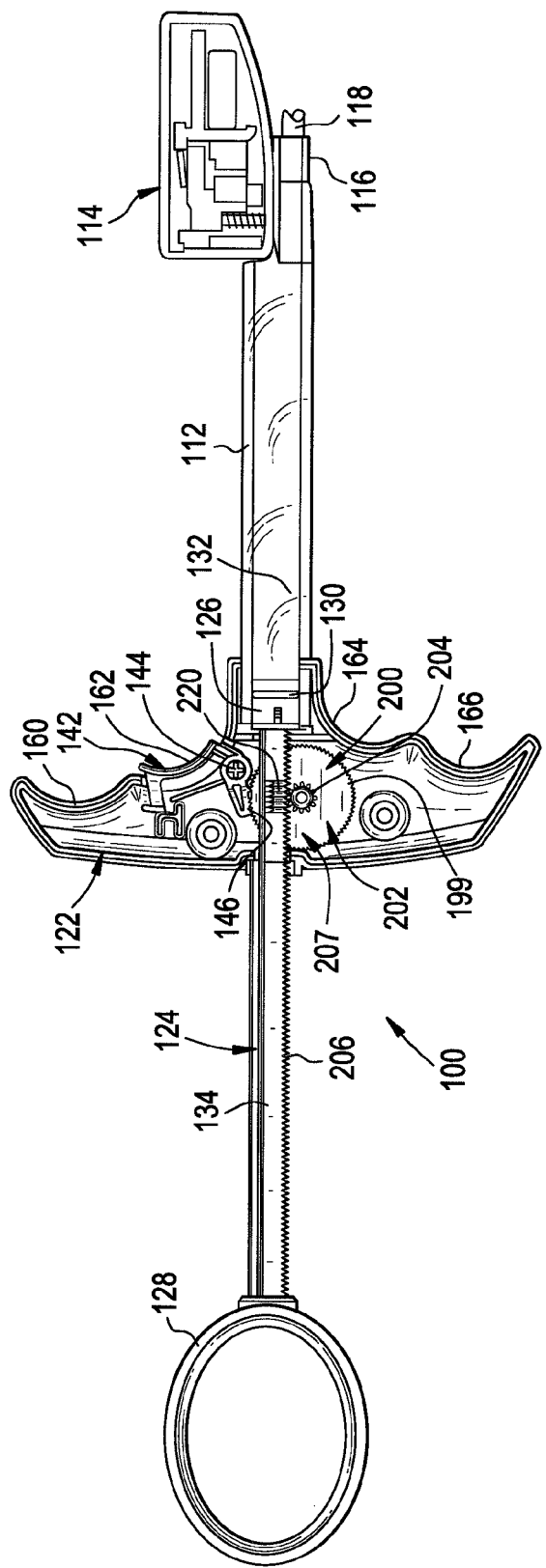
FIG. 17 shows the inflator of FIGS. 13-16, with the plunger fully retracted, but not rotated into a locked position.
Figure 18:
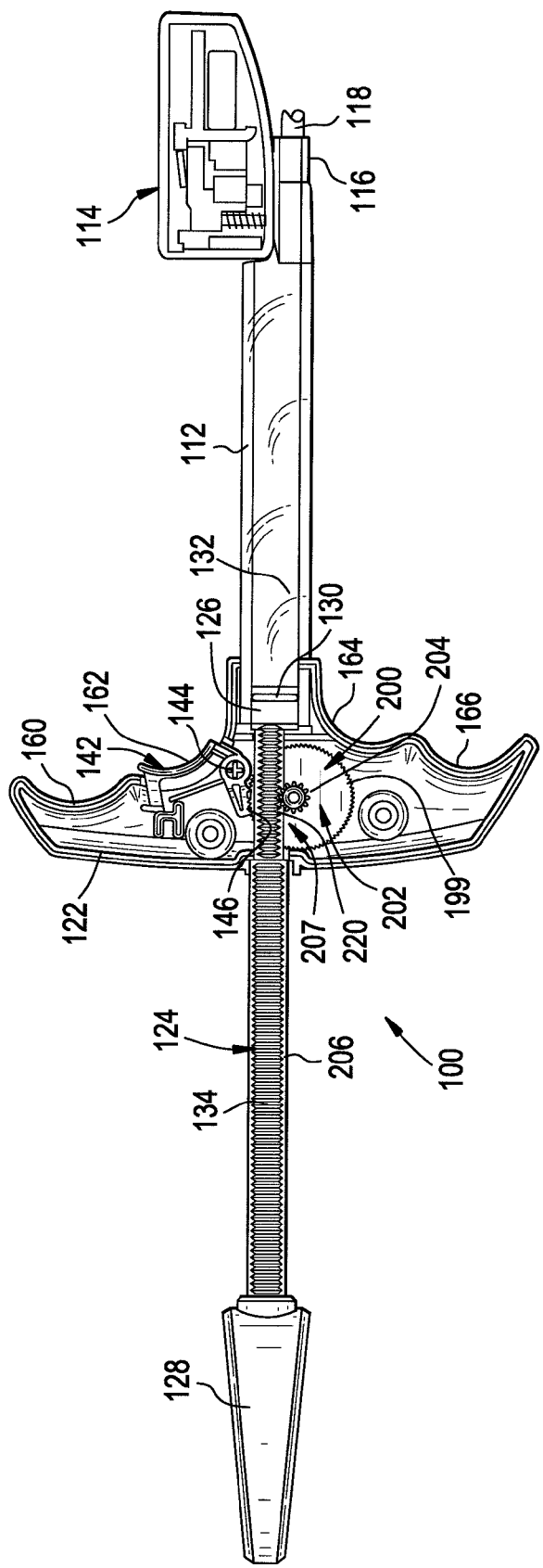
FIG. 18 is similar to FIG. 17, but shows the inflator after the plunger has been rotated into the locked position.

The inflator 100 will now be described in detail. Like the inflator 10 previously described, as shown in FIGS. 17 and 18, the inflator 100 includes a syringe body 112 which is configured to engage a pressure gauge 114 at its end 116 (in the interest of simplifying the training required for users, the unique gauge dial face 70 illustrated in FIG. 12 and previously described can be used), and preferably that same end 116 of the syringe body 112 is also configured to engage a delivery hose 118 which has a Luer connector 120 (such as is shown in FIGS. 2-4) at its end. Alternatively or additionally, the syringe body 112 can be configured to directly receive a Luer connector without having to use the hose 118. Regardless of whether a hose 118 is used, the Luer connector can be engaged with a medical device which is to be inflated, such as a dilation balloon. Although the present description uses sinuplasty as an example application, other procedures where the inflator 100 would serve well include discography, a non-balloon direct injection procedure, and the injection of stem cell material into bodies for tissue repair.

The syringe body 112 extends from, and is connected to, a handle 122. The handle 122 may comprise two halves—a right half 123 and a left half 125 (where the two halves 123, 125 of the handle, when pieced together, form the handle 122 which is effectively hollow). A plunger 124 extends through the handle 122 into the syringe body 112. The plunger 124 has a piston 126 on one end thereof, and a plunger ring 128 is provided at its opposite end. Preferably, a seal 130 is provided on the piston 126, for sealing against an internal wall 132 of the syringe body 112. Between the plunger ring 128 and the end of the plunger 124 extends a rod-like portion 134. The rod-like portion 134 of the plunger 124 preferably includes a gear rack portion 206 as well as a circumferential gear tooth form 220.

A plunger locking mechanism 140 is provided in association with the handle 122 for selectively locking the plunger 124 in place relative to the syringe body 112, with regard to retraction of the plunger 124, while allowing the plunger 124 to be pushed in (i.e., during pressurization). The plunger locking mechanism 140 comprises an actuation lever 142 which is accessible by a user, whereby pressing the actuation lever 142 causes the actuation lever 142 to pivot about pivot point 144 (compare FIG. 15 to FIG. 16). The plunger locking mechanism 140 also has portions which are fully within the handle 122. The actuation lever 142 includes a ratchet pawl 146 which is inside the handle 122, and which is configured to engage ratchet teeth 199 which are provided on a ratchet wheel 200 of a geared ratchet 202 (see FIG. 16). The geared ratchet 202 also includes a pinion 204 which engages a gear rack portion 206 of the plunger 124 (see FIG. 13). As such, the actuation lever 142 and the plunger 124 are effectively linked together, where when the actuation lever 142 is pressed, the ratchet pawl 146 engages the ratchet wheel 200, thereby locking the plunger 124 in place relative to retraction of the plunger 124 but allowing advancement of the plunger 124 (i.e., for pressurization).

The handle 122 supports the geared ratchet 202 via an axle journal 210 (see FIGS. 13 and 14) provided on one side of the geared ratchet 202 engaging in a corresponding axle bearing 222 in the handle 122 (see FIG. 14), and a bearing 212 provided on the opposite side of the geared ratchet 202 (see FIG. 14) engaging corresponding structure in the handle 122.

Preferably, the ratchet wheel 200 has fifty-nine ratchet teeth 199 thereon (although the ratchet wheel 200 can have more or fewer ratchet teeth while still staying within the scope of the present invention). The inflator 100 is configured such that the geared ratchet 202 rotates whenever the plunger 124 traverses within the inflator 100. Although the ratchet teeth 199 may be no smaller than the ratchet teeth that are provided on plunger ratchet 36 on the plunger 24 with regard to inflator 10, one revolution of the geared ratchet 202 of the inflator 100 preferably provides fifty-nine points of engagement for every 0.59 inches of plunger travel compared to inflator 10 that offers 14.75 ratchet teeth over the same distance. The geared ratchet 202 of the inflator 100, therefore, provides four times the number of engagements of those available on a device such as inflator 10 having a ratchet directly on its plunger at 25 percent of load on the engaged ratchet elements.

The actuation lever 142 also includes an integral lever return spring 148. As shown in FIG. 16, when the actuation lever 142 is pressed, causing the actuation lever 142 to pivot about pivot point 144, the integral lever return spring 148 is configured to engage a return spring support 150 or other suitable surface of the handle 122, which causes the integral lever return spring 148 to deflect, effectively urging the ratchet pawl 146 away from the ratchet wheel 200 should the user release the actuation lever 142. The actuation lever 142 also includes an actuating lever travel stop 152 which contacts a lever stop 153 inside the handle 122, which prevents over-pressing of the actuation lever 142.

Figure 19:
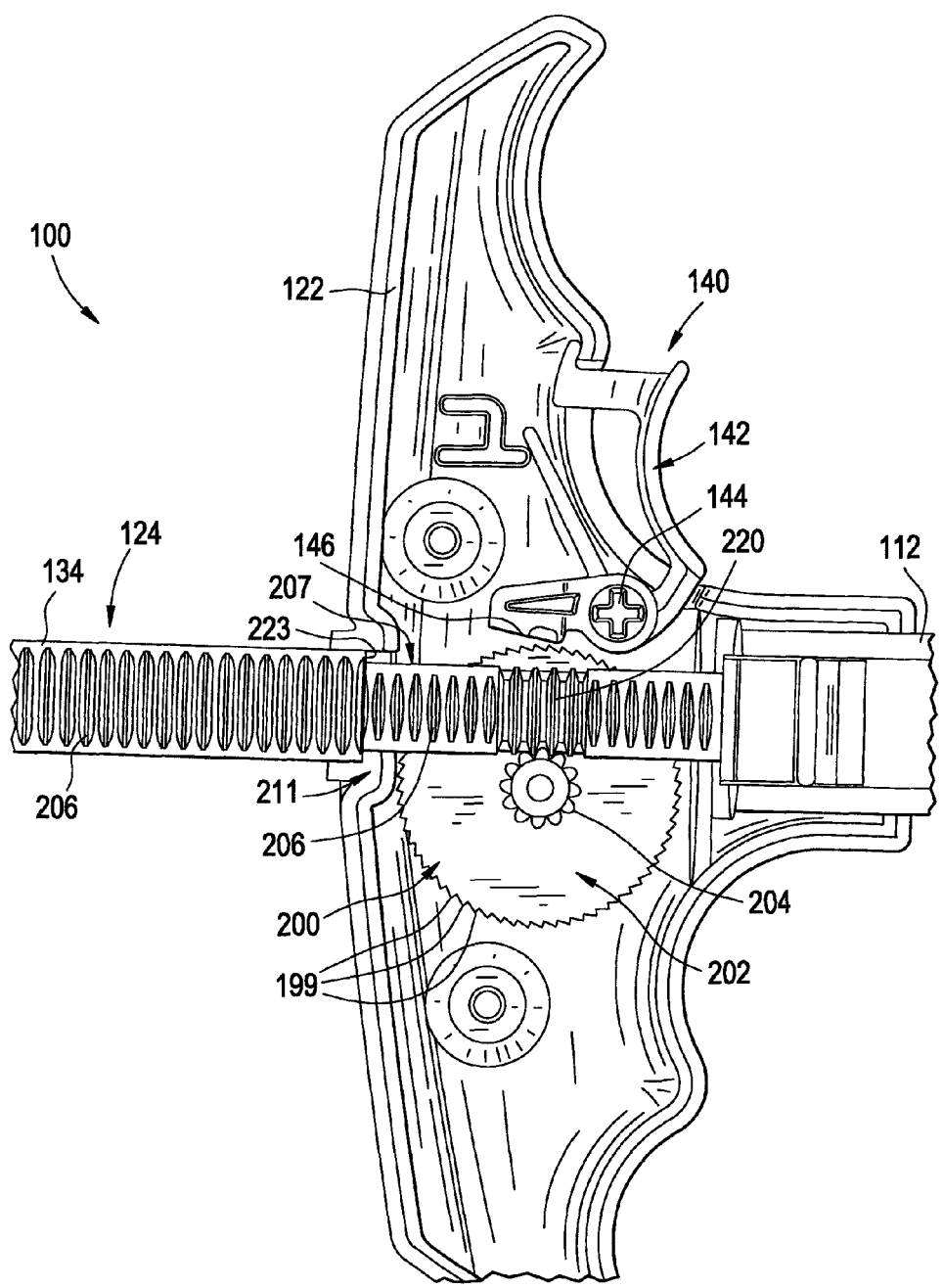
FIG. 19 provides an enlarged view of a portion of the inflator, in the condition where the plunger has been rotated into the locked position.

With regard to an outside contour of the handle 122, as shown in FIGS. 17-19, preferably the handle 122 of the inflator 100 is similar to the handle 22 of the inflator 10, and includes a plurality of indentations 160, 162, 164, 166 for engagement by the fingers of a user. As with the inflator 10, preferably the actuation lever 142 of the inflator 100 is provided in the second indentation 162.

In use, as shown in FIG. 15, the plunger locking mechanism 140 is passive in that it is normally not deployed, but becomes automatically deployed whenever the user's thumb has engaged the plunger ring 128, and a user's finger has engaged the actuation lever 142, in preparation for pressure generation. When the actuation lever 142 is depressed, the actuation lever 142 pivots about pivot point 144, causing the ratchet pawl 146 to engage the ratchet wheel 200, thereby locking the plunger 124 in place as shown in FIG. 16. In this position, the plunger 124 is prevented from retracting, but the plunger 124 can be advanced (pushed in) to increase pressurization. Once achieved, maximum balloon dilation pressure can be sustained for an extended period of time, for example ten seconds or more, without user fatigue simply by maintaining minimal force against the actuation lever 142.

As shown in FIG. 16, in addition to the deflectable leaf spring mounted ratchet pawl 146 engaging the ratchet wheel 200, the integral lever return spring 148 engages a wall or other surface 150 in the handle 22, causing the integral lever return spring 148 to deflect. Upon releasing the actuation lever 142, the integral lever return spring 148 provides the necessary force to restore the actuation lever 142 to its unlocked position as shown in FIG. 15. In order to prevent over-pressing of the actuation lever 142, the actuation lever 142 is provided with a travel stop 152 which contacts a lever stop 153 which is provided in the handle 122 as shown in FIG. 16.

Preferably, the inflator 100 provides a locking feature as is provided with inflator 10 to facilitate balloon deflations. To achieve full balloon deflation following an extended balloon inflation period, the plunger ring 128 may be grasped with a finger, pulled to its fully distal position and the plunger 124 locked in that position by rotating the plunger ring 128 up to 180 degrees (compare FIG. 17 which shows the inflator 100 unlocked, to FIG. 18 which shows the plunger ring 124 having been rotated and the inflator 100 in the locked position). This distal locking feature relieves the user of having to manually hold the plunger 124 in position for the duration of time necessary to achieve full deflation, and frees them entirely to proceed with other aspects of the procedure such as balloon repositioning or removal from the patient.

With regard to the structure which provides this type of locking feature, one possibility is to provide, as shown in FIGS. 17-19, the plunger 124 as having a reduced outside diameter portion 207 which not only includes a portion of the gear rack portion 206, but also includes a circumferential gear tooth form 220. Throughout most of its travel, the plunger 124 is guided by and prevented from rotating by engagement of the pinion 204 of the geared ratchet 202 with the gear rack portion 206 of the plunger 124 as well as a plunger guide and retaining ledge portion 211 (see FIG. 19) of the handle 122. In order to allow locking rotation of the fully distally-positioned plunger, and simultaneously maintain gear tooth registration with the pinion 204 of the geared ratchet 202, the circumferential gear tooth form 220 is provided around at least half of the plunger's reduced diameter portion 207. Releasing the plunger 124 from its distally locked position requires that the plunger 124 first be rotated (via the plunger ring 128) to realign its gear rack portion 206 with the flats of the handle guide and retaining ledges 211 before the plunger 124 can be advanced distally. This action first places the plunger 124 and the pinion 204 of the geared ratchet 202 in proper alignment in order to allow the gear rack portion 206 of the plunger 124 and the pinion 204 of the geared ratchet 202 to be fully reengaged.

With regard to the plunger guide and retaining ledge portion 211, the structure can be provided as similar to what was previously described with regard to inflator 10, wherein either a "rectangular" or "D" shaped cross-section, and wherein one flat (or the only flat) in the "D" shape is faced with the gear rack portion 206 of the plunger 124. Preferably, the plunger 124 extends out of the handle 122 through a close fitting, correspondingly shaped (i.e., either a rectangular or "D"-shaped) hole. Preferably, the far end of the plunger 124 (i.e., the end proximate the piston 126) is cylindrical, with the outside diameter being either the smallest dimension of the rectangular plunger section or, in the case of the "D" shape, of a diameter that when concentric with the with the radius of the "D" form, does not rise up beyond the flat of the "D" form. This cylindrical shape is preferably provided as being long enough such that when the plunger 124 is pulled fully back proximally in the vacuum mode, the beginning of the rectangle or the "D" form of the plunger 124 occurs just outside of the receiving hole in the back of the handle 122. Thereafter, rotating the plunger 124 (via the plunger ring 128) causes the distal corners of the rectangular form or "D" shape to span the minor dimension of the receiving hole in the handle 122, thereby effectively hooking the plunger 124 there, in the position shown in FIGS. 18 and 19, out of registration, until the plunger 124 is rotated back into registration with the receiving hole. In this position, the plunger guide and retaining ledge portion 211 of the handle 122 prevents a shoulder 223 from entering in the handle 122.

While specific embodiments of the invention have been shown and described, it is envisioned that those skilled in the art may devise various modifications without departing from the spirit and scope of the present invention.

What is claimed is:

1. An inflator comprising: a syringe body; a handle on the syringe body; a plunger which extends out from the handle and extends into the syringe body; and a plunger locking mechanism which is associated with the handle, said plunger locking mechanism comprising an actuation lever which is configured to be depressed, thereby causing the plunger locking mechanism to actuate, said plunger locking mechanism comprising a locking structure which is configured to selectively engage corresponding structure on either the plunger or a ratchet wheel which is engaged with the plunger, wherein the inflator is configured such that, when the actuation lever is depressed, the plunger is non-retractable relative to the syringe body, but is pushable into the syringe body to provide advancement relative to the syringe body.

2. An inflator as recited in claim 1, wherein the locking structure of the plunger locking mechanism comprises a ratchet pawl which engages a geared ratchet of the ratchet wheel.

3. An inflator as recited in claim 2, wherein the ratchet wheel comprises a pinion which engages the plunger.

4. An inflator as recited in claim 2, wherein the plunger comprises a gear rack portion and a circumferential gear tooth form.

5. An inflator as recited in claim 2, wherein the handle supports the geared ratchet via an axle journal provided on one side of the geared ratchet engaging in a corresponding axle bearing in the handle, and a bearing provided on an opposite side of the geared ratchet engaging corresponding structure in the handle.

6. An inflator as recited in claim 2, wherein the ratchet wheel has at least fifty-nine ratchet teeth.

7. An inflator as recited in claim 1, wherein the plunger has a piston on a first end, and a plunger ring on a second end.

8. An inflator as recited in claim 7, further comprising a seal on the piston configured to seal against an internal wall of the syringe body.

9. An inflator as recited in claim 1, wherein the plunger locking mechanism comprises an actuation lever, wherein the actuation lever is pressable thereby causing the actuation lever to pivot about a pivot point.

10. An inflator as recited in claim 9, wherein the actuation lever comprises an integral lever return spring which is configured to deflect, wherein the integral lever return spring is configured to urge the ratchet pawl away from the ratchet wheel upon release of the actuation lever.

11. An inflator as recited in claim 10, wherein the actuation lever comprises an actuating lever travel stop which is configured to contact a lever stop disposed in the handle, thereby preventing over-pressing of the actuation lever.

12. An inflator as recited in claim 1, wherein the plunger is rotatable to lock the plunger in place relative to the syringe body.

13. An inflator as recited in claim 12, wherein the plunger comprises a reduced outside diameter portion which comprises a gear rack portion and a circumferential gear tooth form.

14. An inflator as recited in claim 13, wherein the circumferential gear tooth form is provided around at least half of a circumference of the reduced diameter portion of the plunger.

15. An inflator as recited in claim 1, wherein the locking structure of the plunger locking mechanism comprises a ratchet pawl which engages a ratchet on the plunger.

16. An inflator as recited in claim 15, wherein the plunger locking mechanism comprises an actuation lever, wherein the actuation lever is pressable thereby causing the actuation lever to pivot about a pivot point.

17. An inflator as recited in claim 16, wherein the actuation lever comprises an integral lever return spring which is configured to deflect, wherein the integral lever return spring is configured to urge the ratchet pawl away from the ratchet on the plunger upon release of the actuation lever.

18. An inflator as recited in claim 15, wherein the plunger is rotatable to lock the plunger in place relative to the syringe body.

19. An inflator as recited in claim 15, wherein the plunger locking mechanism comprises a pawl disengagement heel which is configured to push against the ratchet pawl and assist moving the ratchet pawl away from the ratchet on the plunger.

* * * * *